United States Patent
Zhu

(10) Patent No.: US 6,399,625 B1
(45) Date of Patent: Jun. 4, 2002

(54) 1-OXORAPAMYCINS

(75) Inventor: Tianmin Zhu, Monroe, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/954,880

(22) Filed: Sep. 18, 2001

Related U.S. Application Data

(60) Provisional application No. 60/235,750, filed on Sep. 27, 2000.

(51) Int. Cl.$^7$ .................. A61K 31/44; C07D 491/16
(52) U.S. Cl. .......................... 514/291; 540/456
(58) Field of Search ................... 540/456; 514/291

(56) References Cited

U.S. PATENT DOCUMENTS

| | | | | |
|---|---|---|---|---|
| 3,929,992 | A | 12/1975 | Sehgal et al. | 424/122 |
| 3,993,749 | A | 11/1976 | Sehgal et al. | 424/122 |
| 4,316,885 | A | 2/1982 | Rakhit | 424/122 |
| 4,401,653 | A | 8/1983 | Eng | 424/114 |
| 4,650,803 | A | 3/1987 | Stella et al. | 514/291 |
| 4,885,171 | A | 12/1989 | Surendra et al. | 424/122 |
| 5,023,263 | A | 6/1991 | Von Burg | 514/291 |
| 5,023,264 | A | 6/1991 | Caulfield et al. | 514/291 |
| 5,078,999 | A | 1/1992 | Warner et al. | 424/122 |
| 5,080,899 | A | 1/1992 | Sturm et al. | 424/122 |
| 5,100,883 | A | 3/1992 | Schiehser | 514/183 |
| 5,100,899 | A | 3/1992 | Calne | 514/291 |
| 5,118,677 | A | 6/1992 | Caufield | 514/183 |
| 5,118,678 | A | 6/1992 | Kao et al. | 514/183 |
| 5,120,842 | A | 6/1992 | Failli et al. | 540/452 |
| 5,130,307 | A | 7/1992 | Failli et al. | 514/321 |
| 5,151,413 | A | 9/1992 | Caufield et al. | 514/63 |
| 5,162,333 | A | 11/1992 | Failli et al. | 514/291 |
| 5,177,203 | A | 1/1993 | Failli et al. | 540/456 |
| 5,206,018 | A | 4/1993 | Sehgal et al. | 424/122 |
| 5,221,670 | A | 6/1993 | Caufield | 514/183 |
| 5,233,036 | A | 8/1993 | Hughes | 540/455 |
| 5,256,790 | A | 10/1993 | Nelson | 514/291 |
| 5,258,389 | A | 11/1993 | Goulet et al. | 514/291 |
| 5,260,300 | A | 11/1993 | Hu | 514/291 |
| 5,262,423 | A | 11/1993 | Kao | 514/291 |
| 5,286,730 | A | 2/1994 | Caufield et al. | 514/291 |
| 5,286,731 | A | 2/1994 | Caufield et al. | 514/296 |
| 5,288,711 | A | 2/1994 | Mitchell et al. | 514/56 |
| 5,302,584 | A | 4/1994 | Kao et al. | 514/80 |
| 5,321,009 | A | 6/1994 | Baeder et al. | 514/4 |
| 5,362,718 | A | 11/1994 | Skotnicki et al. | 514/63 |
| 5,373,014 | A | 12/1994 | Failli et al. | 514/291 |
| 5,378,836 | A | 1/1995 | Kao et al. | 540/456 |
| 5,385,908 | A | 1/1995 | Nelson et al. | 514/291 |
| 5,385,909 | A | 1/1995 | Nelson et al. | 514/291 |
| 5,385,910 | A | 1/1995 | Ocain et al. | 514/291 |
| 5,387,589 | A | 2/1995 | Kulkarni | 514/291 |
| 5,389,639 | A | 2/1995 | Failli et al. | 514/291 |
| 5,391,730 | A | 2/1995 | Skotnicki et al. | 540/456 |
| 5,411,967 | A | 5/1995 | Kao et al. | 514/291 |
| 5,434,260 | A | 7/1995 | Skotnicki et al. | 514/291 |
| 5,463,048 | A | 10/1995 | Skotnicki et al. | 540/456 |
| 5,480,988 | A | 1/1996 | Failli et al. | 540/456 |
| 5,480,989 | A | 1/1996 | Kao et al. | 540/456 |
| 5,489,680 | A | 2/1996 | Failli et al. | 540/456 |
| 5,491,231 | A | 2/1996 | Nelson et al. | 540/456 |
| 5,496,832 | A | 3/1996 | Armstrong | 514/291 |
| 5,504,091 | A | 4/1996 | Molnar-Kimber et al. | 514/291 |
| 5,516,770 | A | 5/1996 | Waranis et al. | 514/183 |
| 5,516,781 | A | 5/1996 | Morris et al. | 514/291 |
| 5,530,006 | A | 6/1996 | Waranis et al. | 514/291 |
| 5,536,729 | A | 7/1996 | Waranis et al. | 514/291 |
| 5,559,121 | A | 9/1996 | Harrison et al. | 514/291 |
| 5,561,138 | A | 10/1996 | Armstrong | 514/291 |
| 5,563,145 | A | 10/1996 | Failli et al. | 514/291 |
| 5,616,588 | A | 4/1997 | Waranis et al. | 514/291 |
| 5,665,772 | A | 9/1997 | Cottens et al. | 514/514 |
| 5,780,462 | A | 7/1998 | Lee et al. | 514/183 |
| 5,985,325 | A | 11/1999 | Nagi | 424/482 |
| 5,989,591 | A | 11/1999 | Nagi | 424/493 |

FOREIGN PATENT DOCUMENTS

EP 0 525 960 A1 2/1993

*Primary Examiner*—Bruck Kifle
(74) *Attorney, Agent, or Firm*—Arnold S. Milowsky

(57) ABSTRACT

This invention provides 1-oxorapamycins, which are useful in inducing immunosuppression, as a neurotrophic agent, and in the treatment of transplantation rejection, autoimmune diseases, solid tumors, fungal infections, and vascular disease.

15 Claims, No Drawings

1-OXORAPAMYCINS

This application claims priority from copending provisional application Serial No. 60/235,750, filed Sep. 27, 2000, the entire disclosure of which is hereby incorporated by reference.

BACKGROUND OF THE INVENTION

This invention relates to 1-oxorapamycins, which are useful in inducing immunosuppression, as a neurotrophic agent, and in the treatment of transplantation rejection, autoimmune diseases, solid tumors, fungal infections, and vascular disease.

Rapamycin is a macrocyclic triene antibiotic produced by *Streptomyces hygroscopius,* which was found to have antifungal activity, particularly against *Candida albicans,* both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephatomyelitis model, a model for multiple sclerosis; in the adjuvant arthritis model, a model for rheumatoid arthritis; and effectively inhibited the formation of lgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

A rapamycin ester, rapamycin 42-ester with 3-hydroxy-2-(hydroxymethyl)-2-methylpropionic acid [disclosed in U.S. Pat. No. 5,362,718], also known as CCI-779, has been shown to have antitumor activity against a variety of tumor cell lines, in in vivo animal tumor models, and in Phase I clinical trials. [Gibbons, J., Proc. Am. Assoc. Can. Res. 40: 301 (1999); Geoerger, B., Proc. Am. Assoc. Can. Res. 40: 603 (1999); Alexandre, J., Proc. Am. Assoc. Can. Res. 40: 613 (1999); and Alexandre, J., Clin. Cancer. Res. 5 (November Supp.): Abstr. 7 (1999)].

DESCRIPTION OF THE INVENTION

This invention provides 1-oxorapamycins, and methods of using them that are described herein. As defined herein, the term "a 1-oxorapamycin" defines a class of immunosuppressive compounds which contain the basic 1-oxorapamycin nucleus (shown below). The 1-oxorapamycins of this invention include compounds which may be chemically or biologically modified as derivatives of the 1-oxorapamycin nucleus, while still retaining immunosuppressive properties. Accordingly, the term "a 1-oxorapamycin" includes esters, ethers, oximes, hydrazones, and hydroxylamines of rapamycin, as well as rapamycins in which functional groups on the rapamycin nucleus have been modified, for example through reduction or oxidation. The term "a 1-oxorapamycin" also includes pharmaceutically acceptable salts of 1-oxorapamycins, which are capable of forming such salts, either by virtue of containing an acidic or basic moiety.

1-OXORAPAMYCIN

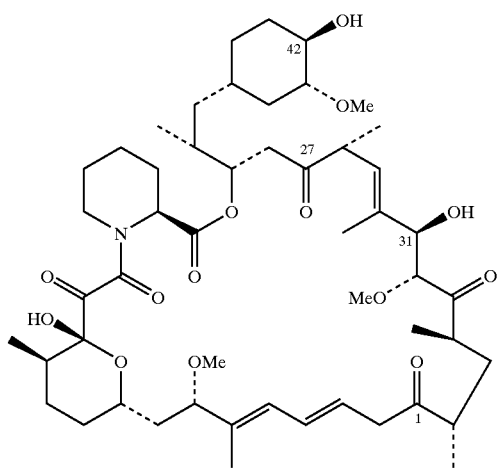

It is preferred that the esters and ethers of 1-oxorapamycin are of the hydroxyl groups at the 42- and/or 31-positions of the 1-oxorapamycin nucleus, esters and ethers of a hydroxyl group at the 27-position (following chemical reduction of the 27-ketone), and that the oximes, hydrazones, and hydroxylamines are of a ketone at the 42-position (following oxidation of the 42-hydroxyl group) and of 27-ketone of the 1-oxorapamycin nucleus.

Preferred 42- and/or 31-esters and ethers of rapamycin are disclosed in the following patents, which are all hereby incorporated by reference: alkyl esters (U.S. Pat. No. 4,316, 885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118, 678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258, 389); carbonate esters (U.S. Pat. No. 5,260,300); arylcarbonyl and alkoxycarbonyl carbamates (U.S. Pat. No. 5,262, 423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463, 048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462). The preparation of these esters and ethers are disclosed in the patents listed above. The preparation of the corresponding esters and ethers of 1-oxorapamycin can be accomplished using the methodology described in these patents, starting with 1-oxorapamycin.

Preferred 27-esters and ethers of rapamycin are disclosed in U.S. Pat. No. 5,256,790, which is hereby incorporated by reference. The preparation of these esters and ethers are disclosed in the patents listed above. The preparation of the corresponding esters and ethers of 1-oxorapamycin can be accomplished using the methodology described in these patents, starting with 1-oxorapamycin.

Preferred oximes, hydrazones, and hydroxylamines of rapamycin are disclosed in U.S. Pat. Nos. 5,373,014, 5,378,836, 5,023,264, and 5,563,145, which are hereby incorporated by reference. The preparation of these oximes, hydrazones, and hydroxylamines are disclosed in the above listed patents. The preparation of 42-oxorapamycin is disclosed in U.S. Pat. No. 5,023,263, which is hereby incorporated by reference. The preparation of the corresponding oximes, hydrazones, and hydroxylamines of 1-oxorapamycin can be accomplished using the methodology described in these patents, starting with 1-oxorapamycin.

Particularly preferred 1-oxorapamycins include 1-oxorapamycin, 1-oxorapamycin 42-ester with 3-hydroxy-2-(hydroxymethyl)-2-methylpropionic acid [see U.S. Pat. No. 5,362,718 for the preparation of rapamycin 42-ester with 3-hydroxy-2-(hydroxymethyl)-2-methylpropionic acid], and 42-O-(2-hydroxy)ethyl 1-oxorapamycin [see U.S. Pat. No. 5,665,772 for the preparation of 42-O-(2-hydroxy) ethyl rapamycin].

When applicable, pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when the rapamycin contains a suitable basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when the rapamycin contains a suitable acidic moiety.

As used in accordance with this invention, the term "providing," with respect to providing a compound or substance covered by this invention, means either directly administering such a compound or substance, or administering a prodrug, derivative, or analog which will form the equivalent amount of the compound or substance within the body.

The compounds of this invention can be made from either commercially available starting materials or from starting materials that can be prepared according to literature procedures. For example, 1-oxorapamycin can be prepared by heating rapamycin in a non-hydrolyzing solvent, and monitoring the progress of the reaction, until the desired product has formed. For example, 1-oxorapamycin can be prepared by heating rapamycin in acetonitrile at 60° C. for 3–7 days.

The antifungal activity for the 1-oxorapamycins of this invention was confirmed in a standard pharmacological test procedure which measured the ability of the compound being evaluated to inhibit fungal growth. 1-Oxorapamycin (Compound I), 1-oxorapamycin 42-ester with 3-hydroxy-2-(hydroxymethyl)-2-methylpropionic acid (Compound II), and 42-O-(2-hydroxy)ethyl 1-oxorapamycin (Compound III) were evaluated as representative compounds of this invention. The procedure used and results obtained are briefly described below. A 96 U-bottom microtiter plate was filled (50 μl/well) with RPMI 1640. The compounds to be evaluated were placed in appropriate wells, and serial diluted in successive wells to provide 11 dilutions. The concentrations ranged from 64 through 0.06 μg/ml. An adjusted inoculum of fungi (50 μl) was added to each well and the plates were incubated at 35° C. for 24–48 hours. The MIC is the lowest concentration of compound which completely inhibited growth of organism in the wells. The following table shows the results obtained in this standard pharmacological test procedure. Where the same fungi is listed more than once, it indicates that more than one strain was evaluated. Nystatin and rapamycin were used for the purpose of comparison.

TABLE 1

ANTIFUNGAL ACTIVITY (MIC in μg/ml)

| Yeast/Fungi | Rapamycin | Compound I | Compound II | Compound III | Nystatin |
|---|---|---|---|---|---|
| C. albicans GC 3065 | 0.50 | 2 | 2 | 2 | 1 |
| C. albicans GC 3064 | <0.12 | 8 | 8 | 4 | 1 |
| C. albicans GC 3066 | <0.12 | 2 | 2 | 2 | 1 |
| C. parapsilosis GC 3075 | <0.12 | 1 | 2 | 2 | 0.50 |
| C. parapsilosis GC 3074 | 0.25 | 2 | 2 | 2 | 1 |
| C. parapsilosis GC 3076 | <0.12 | 2 | 1 | 2 | 0.50 |
| C. pseudotropicalis 3070 | <0.12 | 0.50 | 0.50 | 2 | 0.50 |
| C. tropicalis GC 3081 | 0.25 | 0.50 | 0.50 | 2 | 1 |
| C. tropicalis GC 3080 | 0.25 | 2 | 1 | 2 | 0.25 |
| C. krussii GC 3067 | 4 | 16 | 16 | >32 | 1 |
| C. lusitaniae GC 3068 | <0.12 | 0.50 | 1 | 2 | 0.50 |
| C. lusitaniae GC 3068 | 0.50 | 2 | 1 | N/A | 1 |
| A. fumigatus GC 3092 | >128 | 64 | 64 | 2 | 1 |
| A. niger GC 3091 | >128 | 64 | 32 | >32 | 2 |
| A. niger GC 6591 | >128 | 64 | 64 | >32 | 2 |

The results obtained in this standard pharmacological test procedure demonstrate that the compounds of this invention are useful as antifungal agents.

Antineoplastic activity for the compounds of this invention was confirmed by evaluating the antineoplastic activity of representative compounds of this invention (Compounds I–III) against six tumor cell lines in vitro. Briefly, tumor cells from six cell lines were placed in wells of a 96 well microtiter plate. The following tumor cell lines were used: 3T3 (ovarian), 3T3/H2N (ovarian—resistant to cis-platin), A431 (vulva epidermoid origin), SW620 (colon), SKBR3 (breast), and MDA-435 (breast). The tumors cells were grown in the presence of serial dilutions of the compound to be evaluated for 48 hours, and cell growth determined using a colorimetric procedure (sulforhrodamine B). The inhibition of growth was calculated compared to the number of cells at the time of test compound addition. Results are expressed as an $IC_{50}$ ($\mu$g/ml); N/A indicates the compound was not evaluated against that cell line. The following $IC_{50}$s was listed on Table 2.

TABLE 2

| | Antineoplastic Activity ($IC_{50}$ in $\mu$g/ml) | | | |
|---|---|---|---|---|
| Cell line | Rapamycin | Compound I | Compound II | Compound III |
| 3T3 | 0.48 | 0.89 | 0.84 | N/A |
| 3T3/H2N | 1.7 | 2.3 | 3.0 | N/A |
| A431 | 1.9 | 6.2 | 5.5 | 0.48 |
| SKBR3 | 0.87 | 3.6 | 1.7 | 0.038 |
| MDA435 | 1.3 | 6.0 | 2.8 | N/A |
| SW620 | 2.3 | 12.7 | 8.7 | 1.9 |

The results of this standard pharmacological test procedure demonstrate that the compounds of this invention are useful as antineoplastic agents. In particular, the compounds of this invention are useful against solid tumors, including sarcomas and carcinomas; and more particularly against astrocytomas, prostate cancer, breast cancer, colon cancer, small cell lung cancer, and ovarian cancer; and adult T-cell leukemia/lymphoma.

The neuroregeneration activity for the compounds of this invention was confirmed in a standard pharmacological test procedure by evaluating 1-oxo-rapamycin (Compound I) as representative compound of this invention, against SH-SY5Y cells in vitro [Gold et al., Exp Neurol 147: 269–278, 1997]. Briefly, SH-SY5Y cells were placed in 6-well plate treated with aphidicolin for 5 days followed by the test compounds using 6-well plates. For controls, wells were untreated, or treated with nerve growth factor (NGF) alone. Test wells were treated with NGF plus compound I or rapamycin. Cells were photographed at 168 hours. Analysis of neuritic lengths was performed on photographic prints using a Houston Instrument HI-PAD digitizing tablet connected to an IBM XT computer with appropriate software (Bioquant IV, R&M Biometrics, Nashville, Tenn.). Mean values for axonal areas were compared using by ANOVA (STATVIEW, Abacus Concepts, Inc., Berkeley, Calif. The following table summarizes the results that were obtained.

TABLE 3

Mean Neurite Lengths after 168 h

| | Neurite Length ($\mu$h) | |
|---|---|---|
| Untreated Cell | 109.5 ± 2.6[a] | (n = 115) |
| NGF | 196.5 ± 7.7* | (n = 112) |
| Rapamycin + NGF | 261.4 ± 13.1** | (n = 119) |
| Compound I + NGF | 233.7 ± 8.8** | (n = 174) |

[a]Values are mean ± SEM (in $\mu$m). n, number of cells.
*$p < 0.05$ compare to Untreated Cell
**$p < 0.05$ compare to NGF and Untreated Cell The results obtained in the standard pharmacological test procedure demonstrated that the compounds of this invention are useful as neurotrophic agents, and are particularly useful in promoting promote neuronal regeneration and functional recovery and to stimulate neurite outgrowth and thereby to treat various neuropathological states, including damage to peripheral nerves and the central nervous system caused by physical injury (e.g., spinal cord injury and trauma, sciatic or facial nerve lesion or injury), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone; ticks, porphyria, Gullain-Barre syndrome, dimentia, Alzheimer's disease, Parkinson's disease, and Huntington's chorea.

The compounds of this invention are also useful treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and ocular uveitis; adult T-cell leukemia/lymphoma; fungal infections; hyperproliferative vascular diseases such as restenosis; graft vascular atherosclerosis; and cardiovascular disease, cerebral vascular disease, and peripheral vascular disease, such as coronary artery disease, cerebrovascular disease, arteriosclerosis, atherosclerosis, nonatheromatous arteriosclerosis, or vascular wall damage from cellular events leading toward immune mediated vascular damage, and inhibiting stroke or multiinfarct dementia.

When used for restenosis, it is preferred that the compounds of this invention are used to treat restenosis that occurs following an angioplasty procedure. When used for this treating restenosis following an angioplasty, the compounds of this invention can be administered prior to the procedure, during the procedure, subsequent to the procedure, or any combination of the above.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, mycophenolate, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

When used in the treatment or inhibition of vascular disease, it is contemplated that a 1-oxorapamycin may be used as the sole active ingredient to provide the cardiovascular, cerebral, or peripheral vascular benefits covered by this invention, or may be administered in combination with other agents which provide beneficial cardiovascular, cerebral, or peripheral vascular effects. Such agents are generally in the classes of compounds known as ACE inhibitors, such as quinapril, perindopril, ramipril, captopril, trandolapril, fosinopril, lisinopril, moexipril, and enalapril; angiotensin II receptor antagonists, such as candesartan, irbesartan, losartan, valsartan, and telmisartan; fibric acid derivatives, such as clofibrate, and gemfibrozil; HMG Co-A reductase inhibitors, such as cerivastatin, fluvastatin, atorvastatin, lovastatin, pravastatin, simvastatin; beta adrenergic blocking agents, such as sotalol, timolol, esmolol, carteolol, propranolol, betaxolol, penbutolol, nadolol, acebutolol, atenolol, metoprolol, and bisoprolol; calcium channel blockers, such as nifedipine, verapamil, nicardipine, diltiazem, nimodipine, amlodipine, felodipine, nisoldipine, and bepridil; antioxidants; anticoagulants such as, warfarin, dalteparin, heparin, enoxaparin, and danaparoid; and agents useful in hormone replacement therapy containing estrogens, such as conjugated estrogens, ethinyl estradiol, 17-beta-estradiol, estradiol, and estropipate.

It is understood that the effective dosage of a 1-oxorapamycin may vary depending upon the particular compound utilized, the mode of administration, the condition, and severity thereof, of the condition being treated, as well as the various physical factors related to the individual being treated. As used in accordance with invention, satisfactory results may be obtained when the 1-oxorapamycin is administered in a daily oral dosage of from about projected daily dosages of active compound would be 0.1 $\mu$g/kg–100 mg/kg, preferably between 0.001–25 mg/kg, and more preferably between 0.01–5 mg/kg. The projected daily dosages are expected to vary with route of administration.

When the 1-oxorapamycin is used as part of a combination regimen, dosages of each of the components of the combination are administered during a desired treatment period. The components of the combination may administered at the same time; either as a unitary dosage form containing both components, or as separate dosage units; the components of the combination can also be administered at different times during during a treatment period, or one may be administered as a pretreatment for the other.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. It is more preferred that poloxamer 188 is used as the surface modifying agent. Oral formulations herein may utilize standard delay or time release formulations to alter the absorption of the active compound(s). Preferred oral formulations of rapamycin is disclosed in U.S. Pat. Nos. 5,559,121; 5,536,729; 5,989,591; and 5,985,325, which are hereby incorporated by reference.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. Preferred parenteral formulations for administering rapamycin are disclosed in U.S. Pat. Nos. 5,530,006; 5,516,770; and 5,616,588, which are hereby incorporated by reference.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The following provides procedures for the preparation of representative compounds of this invention.

EXAMPLE 1

1-Oxo-rapamycin (Compound I)

Rapamycin (1.0 g, 1.1 mmole) was dissolved in the acetonitrile and heated 7 days in oil bath at 60° C. The crude product was purified by preparative HPLC on a Prep Nova-pak HR C18 column (300×19 mm) using gradient method that held 65% A and 35% B for the first 5 min then changed from 65% A and 35% B to 10% A and 90% B in 30 min. Buffer A consisted of 90% water and 10% acetonitrile. Buffer B consisted of 10% water and 90% acetonitrile. The flow rate was 20 mL/min. The fraction at 25 min was collected and extracted with methylene chloride. The organic layer was dried with anhydrous sodium sulfate. The organic solvent was removed using a rotary evaporation system. The residual was dissolved in 1 mL methylene chloride and precipitated by adding 7 mL hexane. After filtration, the white solid was dried in the speed-vac overnight. The crude product was also purified by 53% B and 47% A on same column. The peak at 23 min was collected, work up again as described above. A white solid was obtained.

TABLE 3

Assignments for Compound I, DMSO-d6, 600 MHz ($^{13}$C: 100 MHz)

| C# | δ $^{13}$C major | δ $^{13}$C minor | δ $^{1}$H major | δ $^{1}$H minor | COSY | HMBC[a] |
|---|---|---|---|---|---|---|
| 1 | 211.51 | 211.46 | | | | H(2, 2', 3, 35, 36, 50) |
| 2 | 44.8 | 43.42 | 3.48 | 3.39 | H(2', 3) | H(3, 4) |
| | | | 3.32 | 3.36 | H(2, 3) | |
| 3 | 126.4 | 126.4 | 5.76 | 5.78 | H(2, 2') | H(2, 2', 4, 5) |
| 4 | 128.8 | 129.1 | 6.37 | 6.38 | H(3, 5) | H(2, 2', 3, 5) |
| 5 | 126.2 | 128.6 | 6.05 | 5.98 | H(4, 45) | H(3, 4, 7, 45) |
| 6 | 136.1 | 134.3 | | | | H(4, 8, 8', 45) |
| 7 | 82.1 | 83.1 | 3.61 | 3.52 | H8 | H(5, 8, 45, 52) |
| 8 | 39.9 | 38.7 | 1.81 | 1.58 | H(7, 9) | H(7) |
| 9 | 66.3 | 66.1 | 3.99 | 3.67 | H(7,10a,e)[b] | H(8, 10, 11) |
| 10 | 30.7 | | 1.33 | | H(8W, 9, 10a) | H(8) |
| | | | 1.21 | | H(9, 10e, 11a) | |
| 11 | 26.3 | 26.4 | 1.55 | | H(11e, 12) | H(12, 46) |
| | | | 1.49 | | H(11a) | |
| 12 | 34.6 | 34.8 | 2.02 | 2.04 | H(11a) | H(46), OH(14) |
| 14 | 98.9 | 99.0 | | | | H(11, 12, 46), OH(14) |
| 14 (OH) | | | 6.36 | 6.44 | | |
| 15 | 198.5 | 198.2 | | | | OH(14) |
| 16 | 169.0 | 168.8 | | | | H(22) |
| 18 | 38.2 | 43.5 | 4.29 (eq) | 3.43 (eq) | H(18a, 19a) | H(22) |
| | | | 2.77 (ax) | 3.05 (ax) | H(18e, 19a, 19e weak) | |
| 19 | 24.4 | 24.0 | 1.71 (eq) | 1.55 (eq) | H(18a, 19a) | H(21) |
| | | | 1.31 (ax) | 1.33 (ax) | H(18e,a, 19e) | |
| 20 | 20.4 | 20.7 | 1.68 (eq) | 1.73 (eq) | H(20a) | H(22) |
| | | | 1.33 (ax) | 1.33 (ax) | H(20e, 21a) | |
| 21 | 26.6 | 27.4 | 2.14 (eq) | 2.09 (eq) | H(21a, 22) | H(22) |
| | | | 1.59 (ax) | 1.70 (ax) | H(20a, 21e, 22) | |
| 22 | 50.9 | 56.0 | 4.96 | 4.32 | H(21a, e) | |
| 23 | 166.8 | 165.9 | | | | H(22) |
| 25 | 73.6 | 75.2 | 5.09 | 5.11 | H(26, 26', 37) | H(26, 26') |
| 26 | 40.1 | | 2.75 | 2.80 | H(25, 26') | |
| | | | 2.58 | 2.55 | H(25, 26) | |
| 27 | 208.0 | 208.4 | | | | H(26, 28, 37, 47) |
| 28 | 45.0 | 45.5 | 3.33 | 3.46 | H(29, 47) | H(29, 47) |
| 29 | 124.5 | 125.9 | 5.20 | 5.32 | H(28, 48) | H(28, 47, 48) |
| 30 | 137.4 | | | | | H(28, 29w, 31, 32, 48), OH(31) |
| 31 | 75.7 | 76.2 | 4.08 | 3.926 | H(32, 48), OH(31) | H(29, 33, 48) |
| 31 (OH) | | | 5.31 | 5.36 | H(31) | |
| 32 | 86.4 | 86.3 | 3.920 | 3.74 | H(31) | H(29, 31, 53) |
| 33 | 210.8 | 212.5 | | | | H(32, 34, 35, 49) |
| 34 | 40.3 | 39.5 | 2.38 | | H(35, 49) | H(35, 49) |
| 35 | 35.4 | 34.9 | 1.85 | 1.85 | H(34, 35') | H(34, 36, 49, 50) |
| | | | 1.05 | 0.91 | H(34, 35) | |
| 36 | 42.9 | 43.1 | 2.74 | 2.65 | H(35, 35', 50) | H(35, 50) |
| 37 | 33.2 | 32.1 | 1.74 | 1.94 | H(38, 38', 51) | H(26, 51) |
| 38 | 38.1 | | 1.00 | | H(38', 39) | |
| | | | 1.11 | | H(38, 39) | |
| 39 | 32.6 | | 1.27 (ax) | 1.28 | H(38, 38', 40a,e, 44a) | H(37, 38, 40) |
| 40 | 35.2 | | 1.93 (eq) | | H(39w, 40a) | |
| | | | 0.60 (ax) | | H(39, 40e) | |
| 41 | 83.7 | | 2.83 (ax) | | H(40a,e, 42) | H(54) |
| 42 | 73.0 | | 3.17 (ax) | | H(41, 43e,a), OH(42) | H(40, 41, 43), OH(42) |
| 42 (OH) | | | 4.58 | 4.57 | H(42) | |
| 43 | 32.9 | | 1.76 (eq) | | H(42, 43a) | |
| | | | 1.16 (ax) | | H(42, 43e, 44a) | |
| 44 | 30.8 | | 1.55 (eq) | | H(44a) | H(38, 39, 40) |
| | | | 0.85 (ax) | | H(39, 43a, 44e) | |
| 45 | 10.1 | 11.0 | 1.55 | 1.63 | H(5) | |

TABLE 3-continued

Assignments for Compound I, DMSO-d6, 600 MHz ($^{13}$C: 100 MHz)

| C# | δ $^{13}$C major | δ $^{13}$C minor | δ $^{1}$H major | δ $^{1}$H minor | COSY | HMBC[a] |
|---|---|---|---|---|---|---|
| 46 | 15.6 | 15.5 | 0.74 | 0.72 | H(12) | |
| 47 | 15.8 | 16.1 | 0.90 | 1.06 | H(28) | |
| 48 | 13.2 | 12.1 | 1.71 | 1.66 | H(29, 31) | |
| 49 | 14.3 | 15.2 | 0.87 | 0.94 | H(34) | |
| 50 | 17.5 | 16.9 | 1.03 | 1.11 | H(36) | |
| 51 | 15.0 | 15.4 | 0.81 | 0.85 | H(37) | |
| 52 | 55.4 | 54.8 | 3.06 | 2.99 | | H(7) |
| 53 | 57.2 | 57.25 | 3.22 | 3.15 | | H(32) |
| 54 | 56.6 | 56.5 | 3.31 | 3.29 | | H(41) |

[a] = protons listed in this column show HMBC correlations to the carbon of the relevant row
[b] = abbreviations: a = axial; e = equatorial; w = weak; W = W-coupling Both the positive and negative ion modes were performed to confirm the molecular of 929 with a strong positive ion at m/z 947 ([M+NH$_4$]$^+$) as well as two negative ions m/z 928 ([M−H]$^−$) and m/z 988 ([M+OAc]$^−$), respectively. Using rapamycin as internal standard, the exact mass of [M+NH4]$^+$ was 947.5884 dalton with elemental composition of C$_{51}$H$_{83}$N$_2$O$_{14}$ (theoretical mass=947.5844 dalton). This value indicated compound containing one extra oxygen atom compared to rapamycin.

MS/MS experiment was used to get structural related fragment ion spectrum. One positive ion of m/z 947 and one negative ion of m/z 928 were fragmented with collision induced dissociation (CID) technique. Since, only negative fragment ions can solve the final proposed structure, the result and data interpretation only cover the negative MS/MS spectrum.

The exact mass measurements for fragment ions were obtained by recalibrate ion mass by using two known ion peaks of m/z 928 and 128. The fragment ions and their best fitting elemental compositions are listed as follows,

| Exact Mass (Dalton) | Elemental Composition | Δ (mDa) |
|---|---|---|
| 928.5422 | C$_{51}$H$_{78}$NO$_{14}$ | Reference 1 |
| 910.5397 | C$_{51}$H$_{76}$NO$_{13}$ | −8.0 |
| 896.5204 | C$_{50}$H$_{74}$NO$_{13}$ | −4.4 |
| 878.5015 | C$_{50}$H$_{72}$NO$_{12}$ | +4.0 |
| 606.3299 | C$_{32}$H$_{48}$NO$_{10}$ | −2.1 |
| 574.3020 | C$_{31}$H$_{44}$NO$_9$ | −0.4 |
| 556.2919 | C$_{31}$H$_{42}$NO$_8$ | −0.9 |
| 530.3124 | C$_{30}$H$_{44}$NO$_7$ | −0.6 |
| 512.3016 | C$_{30}$H$_{42}$NO$_6$ | −0.4 |
| 342.2083 | C$_{21}$H$_{28}$NO$_3$ | −1.4 |
| 321.2066 | C$_{19}$H$_{29}$O$_4$ | −0.6 |
| 303.1973 | C$_{19}$H$_{27}$O$_3$ | −1.3 |
| 277.1814 | C$_{17}$H$_{25}$O$_3$ | −1.0 |
| 168.0667 | C$_8$H$_{10}$NO$_3$ | −0.6 |
| 163.1144 | C$_{11}$H$_{15}$O | −2.1 |
| 128.0712 | C$_6$H$_{10}$NO$_2$ | Reference 2 |
| 107.0875 | C$_6$H$_{11}$ | −1.4 |

EXAMPLE 2

1-Oxorapamycin 42-ester with 3-Hydroxy-2-(hydroxymethyl)-2-methylpropionic acid (Compound II)

Rapamycin 42-ester with 3-Hydroxy-2-(hydroxymethyl)-2-methylpropionic acid (0.8 g, 0.78 mmole) was dissolved in the acetonitrile and heated 4 days in oil bath at 60° C. The crude product was purified by preparative HPLC on a Prep Nova-pak HR C18 column (300×19 mm) using gradient method that held 65% A and 35% B for the first 5 min then changed from 65% A and 35% B to 10% A and 90% B in 30 min. Buffer A consisted of 90% water and 10% acetonitrile. Buffer B consisted of 10% water and 90% acetonitrile. The flow rate was 20 mL/min. The fraction at 25 min was collected and extracted with methylene chloride. The organic layer was dried with anhydrous sodium sulfate. The organic solvent was removed using a rotary evaporation system. The residual was dissolved in 1 mL methylene chloride and precipitated by adding 7 mL hexane. After filtration, the white solid was dried in the speed-vac overnight. The crude product was also purified by 53% B and 47% A on same column. The peak at 23 min was collected, work up again as described above. A white solid was obtained.

TABLE 4

Assignments for compound II in DMSO-d6, 600 MHz ($^{13}$C: 100 MHz)

| C# | δ $^{13}$C major | δ $^{13}$C minor | δ $^{1}$H major | δ $^{1}$H minor |
|---|---|---|---|---|
| 1 | 211.51 | | | |
| 2 | 44.8 | 43.5 | 3.47 | 3.43 |
| | | | 3.32 | 3.40 |
| 3 | 126.4 | | 5.77 | 5.75 |
| 4 | 128.8 | 129.1 | 6.35 | 6.39 |
| 5 | 126.3 | 128.5 | 6.05 | 5.98 |
| 6 | 136.1 | 134.3 | | |
| 7 | 82.0 | | 3.61 | |
| 8 | 39.8 | 38.7 | 1.81 | |
| | | 1.32 | | |
| 9 | 66.3 | 66.1 | 3.98 | 3.67 |
| 10 | 29.3 | | 1.20 | |
| 11 | 26.3 | | 1.53 | |
| | | 1.49 | | |
| 12 | 34.6 | 34.8 | 2.05 | 2.02 |
| 14 | 98.9 | | | |
| 14 (OH) | | | 6.37 | 6.44 |
| 15 | 198.5 | | | |
| 16 | 169.0 | 168.8 | | |
| 18 | 38.2 | 43.5 | 4.29 (eq) | 3.43(eq) |
| | | | 2.78 (ax) | 3.05(ax) |
| 19 | 24.3 | 24.0 | 1.55 (eq) | 1.55(eq) |
| | | | 1.29 (ax) | 1.31(ax) |
| 20 | 20.4 | 20.7 | 1.67 (eq) | |
| | | | 1.31 (ax) | |
| 21 | 26.6 | 27.3 | 2.15 (eq) | 2.09(eq) |
| | | | 1.59 (ax) | 1.71(ax) |
| 22 | 50.9 | 56.0 | 4.97 | 4.33 |
| 23 | 166.9 | | | |
| 25 | 73.6 | 75.1 | 5.10 | 5.11 |

TABLE 4-continued

Assignments for compound II in DMSO-d6, 600 MHz ($^{13}$C: 100 MHz)

| C# | δ $^{13}$C major | δ $^{13}$C minor | δ $^{1}$H major | δ $^{1}$H minor |
|---|---|---|---|---|
| 26 | 40.2 | | 2.76 | |
|  |  |  | 2.56 |  |
| 27 | 208.0 | 208.4 | | |
| 28 | 45.6 | | 3.33 | |
| 29 | 124.5 | 125.8 | 5.20 | 5.33 |
| 30 | 137.4 | | | |
| 31 | 75.7 | 76.1 | 4.08 | 3.93 |
| 31 (OH) | | | 5.31 | 5.35 |
| 32 | 86.4 | 86.2 | 3.93 | 3.73 |
| 33 | 210.7 | 212.4 | | |
| 34 | 40.3 | 39.6 | 2.38 | |
| 35 | 35.0 | | 1.84 | |
|  |  |  | 0.91 |  |
| 36 | 42.8 | 43.2 | 2.74 | 2.69 |
| 37 | 33.3 | | 1.72 | 1.95 |
| 38 | 37.9 | | 1.02 | |
|  |  |  | 1.14 |  |
| 39 | 32.1 | | 1.37 (ax) | 1.24 |
| 40 | 35.7 | | 1.99 (eq) | |
|  |  |  | 0.75 (ax) |  |
| 41 | 80.2 | | 3.17 | |
| 42 | 75.7 | | 4.49 | |
| 43 | 29.2 | | 1.83 (eq) | |
|  |  |  | 1.24 (ax) |  |
| 44 | 30.5 | | 1.59 (eq) | |
|  |  |  | 0.92 (ax) |  |
| 45 | 10.9 | 9.9 | 1.55 | 1.63 |
| 46 | 15.56 | 15.4 | 0.74 | 0.72 |
| 47 | 15.8 | 16.2 | 0.90 | 1.06 |
| 48 | 13.2 | 12.0 | 1.71 | 1.66 |
| 49 | 13.9 | | 0.87 | |
| 50 | 17.5 | 16.9 | 1.03 | 1.11 |
| 51 | 15.1 | 15.3 | 0.81 | 0.86 |
| 52 | 55.4 | 54.8 | 3.06 | 2.99 |
| 53 | 57.2 | 57.0 | 3.22 | 3.16 |
| 54 | 57.1 | 57.0 | 3.29 | 3.27 |
| 55 | 174.15 | 174.12 | | |
| 56 | 49.8 | | | |
| 57 | 63.5 | | 3.47 | |
| 58 | 16.8 | | 1.03 | |

The electrospray with the negative ion mode was performed to show a strong ion peak at m/z 1044. Using rapamycin 42-ester with 3-Hydroxy-2-(hydroxymethyl)-2-methylpropionic acid [M–H]$^-$ ion (m/z 1028) as an internal standard, the high resolution exact mass was measured as 1044.5872 dalton which had the elemental composition of $C_{56}H_{86}NO_{17}$ (theoretical mass=1044.5896). To compare with CCI-779, the compound contains one extra oxygen atom.

MS/MS collision induced dissociation (CID) technique was used to obtain the fragmentation spectrum for m/z 1044 ion. The original spectrum was re-calibrated by choosing two known reference peaks (m/z 128 and m/z 1044). The following list exact mass measurements and their corresponding elemental compositions for MS/MS fragment ions.

| Exact Mass (Dalton) | Elemental Composition | Δ (mDa) |
|---|---|---|
| 1044.5896 | $C_{56}H_{86}NO_{17}$ | Reference 1 |
| 1026.5787 | $C_{56}H_{84}NO_{16}$ | +0.3 |
| 1012.5535 | $C_{55}H_{82}NO_{16}$ | +9.9 |
| 994.5482 | $C_{55}H_{80}NO_{15}$ | +4.6 |
| 606.3286 | $C_{32}H_{48}NO_{10}$ | −0.8 |
| 574.3009 | $C_{31}H_{44}NO_{9}$ | +0.7 |
| 556.2935 | $C_{31}H_{42}NO_{8}$ | −2.5 |
| 530.3126 | $C_{30}H_{44}NO_{7}$ | −0.8 |
| 512.3017 | $C_{30}H_{42}NO_{6}$ | −0.5 |
| 437.2544 | $C_{24}H_{37}O_{7}$ | −0.5 |
| 342.2083 | $C_{21}H_{28}NO_{3}$ | −1.4 |
| 277.1802 | $C_{17}H_{25}O_{3}$ | +0.2 |
| 168.0667 | $C_{8}H_{10}NO_{3}$ | −0.6 |
| 163.1139 | $C_{11}H_{15}O$ | −1.6 |
| 128.0712 | $C_{6}H_{10}NO_{2}$ | Reference 2 |
| 107.0857 | $C_{8}H_{11}$ | +0.4 |

EXAMPLE 3

42-O-(2-Hydroxy)ethyl 1-oxorapamycin (Compound III)

42-O-(2-hydroxy)ethyl rapamycin (35 mg, 0.037 mmole) was dissolved in the 20 mL acetonitrile and heated 3 days in oil bath at 60° C. The crude product was purified by preparative HPLC on a Prep Nova-pak HR C18 column (300×19 mm) using gradient method that held 65% A and 35% B for the first 5 min then changed from 65% A and 35% B to 10% A and 90% B in 30min. Buffer A consisted of 90% water and 10% acetonitrile. Buffer B consisted of 10% water and 90% acetonitrile. The flow rate was 20 mL/min. The fraction at 27.9 min was collected and extracted with methylene chloride. The organic layer was dried with anhydrous sodium sulfate. The organic solvent was removed using a rotary evaporation system. The residual was dissolved in 1 mL methylene chloride and precipitated by adding 7 mL hexane. A white solid was obtained.

TABLE 5

Assignments for Compound III DMSO-d6, 400 MHz

| C# | δ $^{1}$H major | δ $^{1}$H minor |
|---|---|---|
| 1 | | |
| 2 | 3.48 | 3.39 |
|  | 3.32 | 3.36 |
| 3 | 5.76 | |
| 4 | 6.37 | 6.38 |
| 5 | 6.05 | 5.96 |
| 6 | | |
| 7 | 3.60 | 3.52 |
| 8 | 1.81 | 1.58 |
| 9 | 3.99 | 3.67 |
| 10 | 1.33 | |
|  | 1.21 |  |
| 11 | 1.55 | |
|  | 1.49 |  |
| 12 | 2.02 | 2.04 |
| 13 | | |
| 14 (OH) | 6.37 | 6.46 |
| 15 | | |
| 16 | | |
| 18 | 4.27 (eq) | |
|  | 2.74 (ax) |  |
| 19 | 1.56 (eq) | |
|  | 1.31 (ax) |  |
| 20 | 1.68 (eq) | |
|  | 1.33 (ax) |  |
| 21 | 2.18 | |
|  | 1.59 |  |
| 22 | 4.96 | 4.30 |
| 23 | | |
| 25 | 5.10 | |
| 26 | 2.75 | |
|  | 2.58 |  |

TABLE 5-continued

Assignments for Compound III DMSO-d6, 400 MHz

| C# | δ $^1$H major | δ $^1$H minor |
|---|---|---|
| 27 | | |
| 28 | 3.33 | 3.46 |
| 29 | 5.19 | |
| 30 | | |
| 31 | 4.07 | |
| 31 (OH) | 5.32 | 5.37 |
| 32 | 4.07 | |
| 33 | | |
| 34 | 2.38 | |
| 35 | 1.85 | |
| | 1.05 | |
| 36 | 2.74 | 2.65 |
| 37 | 1.74 | 1.94 |
| 38 | | |
| 39 | 1.27 | 1.28 |
| 40 | 1.94 | |
| | 0.64 | |
| 41 | | |
| 42 | 3.17 | |
| 43 | 1.76 (eq) | |
| | 1.16 (ax) | |
| 44 | | |
| 45 | 1.55 | 1.63 |
| 46 | 0.74 | 0.72 |
| 47 | 0.90 | 1.06 |
| 48 | 1.71 | 1.66 |
| 49 | 0.87 | 0.94 |
| 50 | 1.03 | 1.09 |
| 51 | 0.81 | 0.85 |
| 52 | 3.06 | 2.99 |
| 53 | 3.21 | 3.16 |
| 54 | 3.31 | 3.29 |
| 55 | 3.3–3.5 | |
| 56 | 3.3–3.5 | |
| 56 (OH) | 4.22 | 4.01 |

The negative ion mode was performed to confirm the molecular weight of 973 with a strong negative ion shown at m/z 972 for Compound III. Using 42-O-(2-hydroxy)ethyl rapamycin as internal standard, the exact mass of [M–H]$^-$ (CompoundIII) was 972.5664 dalton with elemental composition of $C_{53}H_{83}N_2O_{15}$ (theoretical mass=972.5684 dalton). This value indicated the compound containing one extra oxygen atom compared to 42-O-(2-hydroxy)ethyl rapamycin.

MS/MS experiment was used to get structural related fragment ion spectrum. The negative ion of m/z 972 was fragmented with the collision induced dissociation (CID) technique. The exact mass measurements for fragment ions were obtained by recalibrating ion mass by using two known ion peaks of m/z 277 and 972. The fragment ions and their best fitting elemental compositions are listed as follows.

| Exact Mass (Dalton) | Elemental Composition | Δ (mDa) |
|---|---|---|
| 972.5684 | $C_{53}H_{82}NO_{15}$ | Reference 1 |
| 940.5393 | $C_{52}H_{78}NO_{14}$ | +2.9 |
| 625.4023 | $C_{38}H_{57}O_7$ | +8.1 |
| 606.3238 | $C_{32}H_{48}NO_{10}$ | +4.0 |
| 574.2941 | $C_{31}H_{44}NO_9$ | +7.5 |
| 530.3004 | $C_{30}H_{44}NO_7$ | +11.4 |
| 512.3018 | $C_{30}H_{42}NO_6$ | −0.6 |
| 365.2351 | $C_{21}H_{33}O_5$ | −2.3 |
| 277.1804 | $C_{17}H_{25}O_3$ | Reference 2 |
| 259.1686 | $C_{17}H_{23}O_2$ | +1.2 |
| 168.0665 | $C_8H_{10}NO_3$ | −0.4 |
| 163* | $C_{11}H_{15}O$ | * |
| 107.0868 | $C_8H_{11}$ | −0.7 |

*Signal too weak to get accurate mass

What is claimed is:

1. A compound which is 1-oxorapamycin.

2. A compound which is 1-oxorapamycin 42-ester with 3-hydroxy-2-(hydroxymethyl)-2-methylpropionic acid.

3. A compound which is 42-O-(2-hydroxy)ethyl 1-oxorapamycin.

4. A method of treating or inhibiting transplant rejection or graft vs. host disease in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

5. A method of treating or inhibiting a solid tumor selected from the group consisting of astrocytoma, prostate cancer, breast cancer, colon cancer, small cell lung cancer, and ovarian cancer in a mammal in need thereof, which comprises providing to said mammal an effective amount of 1-oxorapamycin, 1-goxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

6. A method of treating or inhibiting a fungal infection in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

7. A method of treating or inhibiting rheumatoid arthritis in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

8. A method of treating or inhibiting multiple sclerosis in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

9. A method of treating or inhibiting restenosis in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

10. A method of treating or inhibiting pulmonary inflammation in a mammal in need thereof, which comprises providing to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

11. A pharmaceutical composition which comprises a 1-oxorapamycin, 1-oxorapamycin 42-ester with 3-hydroxy- 2-(hydroxymethyl)-2-methylpropionic acid, 42-O-(2-hydroxy)ethyl 1-oxorapamycin, or a pharmaceutically acceptable salt thereof and a pharmaceutical carrier.

12. A method of stimulating the growth of damaged peripheral nerves in a mammal in need thereof, which comprises providing said mammal with an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

13. A method of treating peripheral nerve damage in a mammal in need thereof, which comprises administering to said mammal an effective amount of 1-oxorapamycin, 1-oxorapamycin 42-ester with 3-hydroxy-2-(hydroxymethyl)-2-methylpropionic acid, 42-O-(2-hydroxy)ethyl 1-oxorapamycin, or a pharmaceutically acceptable salt thereof.

14. The method according to claim 13 wherein the peripheral nerve damage is caused by a physical injury or trauma.

15. The method according to claim 14, wherein the peripheral nerve damage is caused by spinal cord injury and trauma, sciatic or facial nerve lesion or injury.

* * * * *